(12) United States Patent
Braz et al.

(10) Patent No.: US 8,117,042 B2
(45) Date of Patent: Feb. 14, 2012

(54) COMMUNICATION AND INTERFACE SUPPORT SYSTEM

(75) Inventors: Matthew Braz, Orlando, FL (US); Venkat Dandibhotla, Collegeville, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1209 days.

(21) Appl. No.: 11/751,828

(22) Filed: May 22, 2007

(65) Prior Publication Data

US 2007/0299688 A1 Dec. 27, 2007

Related U.S. Application Data

(60) Provisional application No. 60/805,494, filed on Jun. 22, 2006.

(51) Int. Cl.
*G06Q 10/00* (2012.01)
*G06Q 50/00* (2012.01)
(52) U.S. Cl. ..................... 705/2; 705/3; 705/4
(58) Field of Classification Search .............. 705/2–3; 709/230, 238
See application file for complete search history.

(56) References Cited

U.S. PATENT DOCUMENTS

| | | | |
|---|---|---|---|
| 6,260,021 B1 | 7/2001 | Wong et al. | |
| 6,757,689 B2 | 6/2004 | Battas et al. | |
| 6,842,906 B1 | 1/2005 | Bowman-Amuah | |
| 6,954,757 B2 | 10/2005 | Zargham et al. | |
| 2005/0240437 A1* | 10/2005 | Cunningham | 705/2 |
| 2006/0007466 A1 | 1/2006 | Ben-Yehuda et al. | |
| 2006/0161840 A1* | 7/2006 | Cohen et al. | 715/513 |
| 2007/0064703 A1 | 3/2007 | Hernandez et al. | |
| 2010/0076783 A1* | 3/2010 | Mathur | 705/2 |

OTHER PUBLICATIONS

McNamara, Health Information Networks: Enabling Care Management in IDSs, Mar. 2000, Healthcare Financial Management.*

* cited by examiner

*Primary Examiner* — Luke Gilligan
(74) *Attorney, Agent, or Firm* — Alexander J Burke

(57) ABSTRACT

A system supports, adaptively processing HL7 compatible transaction message data of different HL7 version as well as conversion of transactions between HL7 versions and operational validation of transaction messages. A system for processing HL7 protocol compatible data comprises an interface for establishing a communication link enabling acquisition of HL7 compatible transaction messages. An acquisition processor acquires multiple different HL7 compatible transaction messages including healthcare data using the communication link. An HL7 data processor automatically parses an HL7 compatible transaction message to identify HL7 items indicating type of information conveyed at a location in the transaction message identified in response to a predetermined message location identifier. The HL7 data processor automatically adaptively routes acquired HL7 compatible transaction messages to multiple different storage destinations based on the identified HL7 items indicating type of information conveyed in response to predetermined information associating HL7 items and type of information conveyed with corresponding storage destinations.

16 Claims, 10 Drawing Sheets

| ACTOR ACTION (923) | SYSTEM RESPONSE (925) |
|---|---|
| USER USES THE HL7 SENDER TO TRANSMIT SAMPLE ON-UNIT LAB RESULTS TO THE INBOUND CONNECTION OF AN INTEGRATION MAP. | INTEGRATION ENGINE ACCEPTS TRANSACTION. |
| | INTEGRATION ENGINE RESPONDS TO TRANSACTION WITH ACK |
| | INTEGRATION ENGINE PROCESSES THE TRANSACTION THROUGH THE INTEGRATION MAP |
| | INTEGRATION ENGINE TRANSMIT MODIFIED TRANSACTION VIA ITS OUTBOUND CONNECTION TO THE HL7 RECEIVER. |
| | HL7 RECEIVER ACCEPTS THE TRANSACTION |
| | HL7 RECEIVER RESPONDS WITH ACK |
| | HL7 RECEIVER WRITES THE TRANSACTION TO DISK, AND DISPLAYS IT IN THE DETAIL VIEW |
| USER USES DETAIL VIEW OF HL7 RECEIVER TO VALIDATE THE TRANSACTION AGAINST EXPECTED RESULTS. | |

FIG. 10

| ACTOR ACTION (933) | SYSTEM RESPONSE (935) |
|---|---|
| USER REFERENCES THE RE-DISTRIBUTABLE API'S AS PART OF APPLICATION CODE TO HANDLE AN INBOUND HL7 INTERFACE | |
| | INBOUND HL7 TRANSACTION IS RECEIVED BY THE APPLICATION |
| THE MESSAGE IN ITS ENTIRELY IS PASSED TO THE API | THE API PARSES THE MESSAGE INTO A HIERARCHICAL OBJECT MODEL |
| | THE API VALIDATES THE MESSAGE FOR COMPLIANCE AGAINST DEFINED MESSAGES, USER DEFINED TEMPLATES, AND USER DEFINED TABLES. |
| | A COLLECTION OF NON-CONFORMING OBJECT REFERENCES IS CREATED. |
| THE APPLICATION CAN REFERENCE DATA EXPECTED IN THE TRANSACTION BY CALLING A METHOD (EITHER BY DESCRIPTION OR POSITION) EX: Object.PID.Patient_Name(0).GivenName OR Object.PID.x5(0).x2 | |

COMMUNICATION AND INTERFACE SUPPORT SYSTEM

This is a non-provisional application of provisional application Ser. No. 60/805,494 filed Jun. 22, 2006, by M. Braz et al.

FIELD OF THE INVENTION

This invention concerns a system for adaptively processing HL7 (HealthLevel 7) protocol compatible data such as transaction messages for communication between different computer systems.

BACKGROUND OF THE INVENTION

It commonly occurs that an HL7 compatible interface needs to be established to be suitable for conveying HL7 transaction messages between different computer systems such as between an ADT (Admission, Discharge and Transfer) system and an ambulatory EMR (Electronic Medical Record) system, for example. Such a created interface needs to be capable of transferring different types of HL7 compatible messages between the different systems without error. Known systems validate an HL7 transaction message for accuracy by typically requiring a user to load a transaction message into a text editor and manually count through message data element delimiters and validate that the data and its placement in each element is correct and conforms to the HL7 standard. This type of burdensome, time consuming validation may occur during the development of an HL7 interface, at the sender, receiver, or in the integration engine or during system operation to verify correct operation perhaps in response to error. Further this burden increases with the complexity and length of transaction message.

There is a need to emulate how data is to be transmitted or received in a real world situation in testing of interfacing logic within an application. For example, test processing of ADT (Admission, Discharge, Transfer) message communication to an ambulatory EMR (Electronic Medical Record) system may involve sending and resending a transaction message multiple times and this may be repeated for different types of messages associated with different scenarios. In known systems such test processing requires substantial user setup time, burdensome manual generation of multiple transaction messages for communication by a sending system as well as initiation of transmission of the generated messages. Known systems are thereby prone to error and reliant on other systems for test data support and the other systems resources may not be available. A system according to invention principles addresses these deficiencies and related problems.

SUMMARY OF THE INVENTION

A system supports, adaptively processing, authoring, editing, transmitting and receiving of HL7 compatible transaction message data of different HL7 version (e.g., 2.x and 3.x versions) as well as conversion of transactions between HL7 versions and operational validation of transaction messages. A system for processing HL7 protocol compatible data comprises an interface for establishing a communication link enabling acquisition of HL7 compatible transaction messages. An acquisition processor acquires multiple different HL7 compatible transaction messages including healthcare data using the communication link. An HL7 data processor automatically parses an HL7 compatible transaction message to identify HL7 items indicating type of information conveyed at a location in the transaction message identified in response to a predetermined message location identifier. The HL7 data processor automatically adaptively routes acquired HL7 compatible transaction messages to multiple different storage destinations based on the identified HL7 items indicating type of information conveyed in response to predetermined information associating HL7 items and type of information conveyed with corresponding storage destinations.

BRIEF DESCRIPTION OF THE DRAWING

FIG. 10 shows system user interactive operations and system response involved in providing and testing an integration engine HL7 message interface between an ambulatory system and a clinical information repository, according to invention principles.

FIG. 11 shows system user interactive operations and system response involved in employing an API in providing and testing an HL7 message interface, according to invention principles.

DETAILED DESCRIPTION OF THE INVENTION

Figure 1:
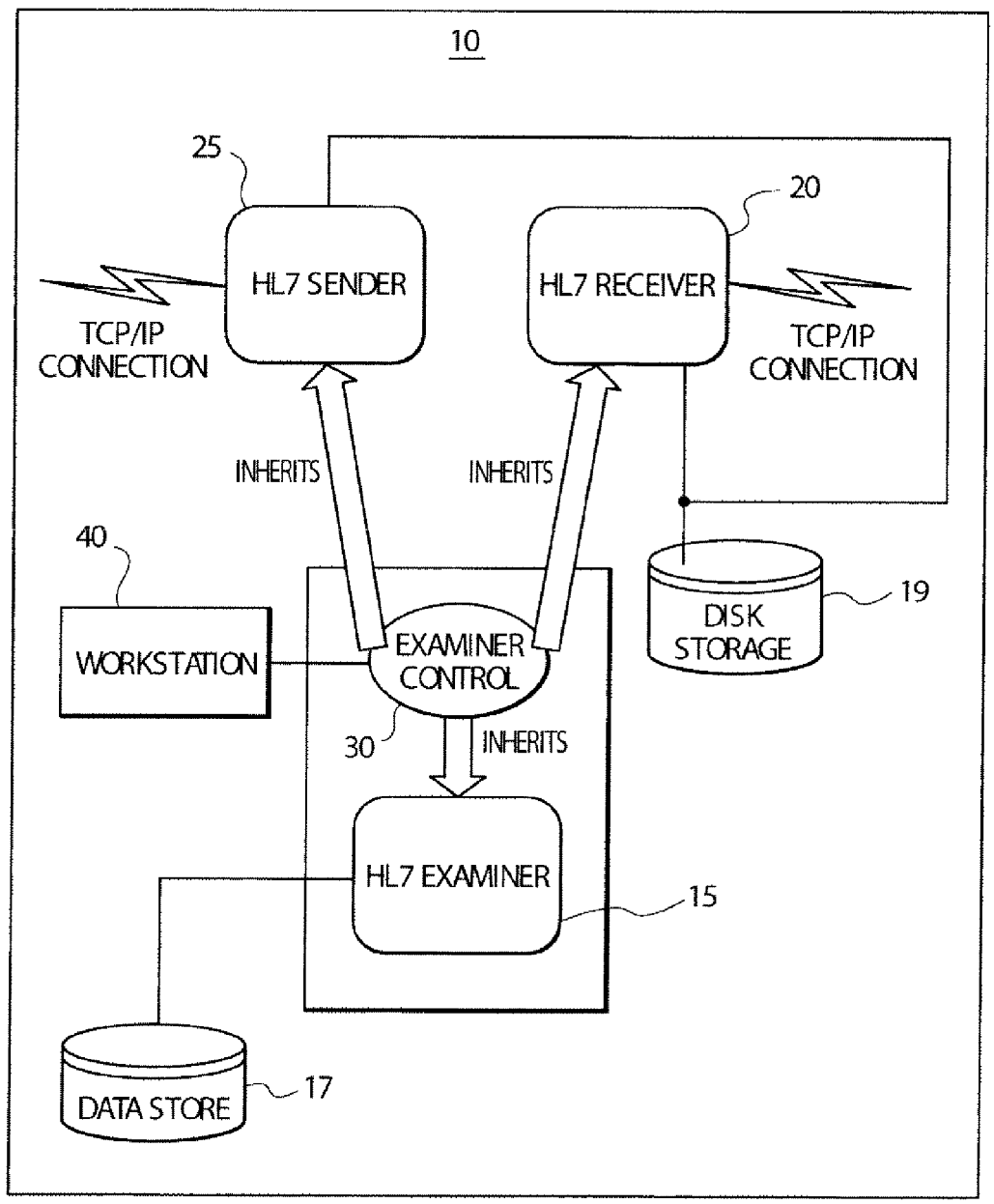
FIG. 1 shows a system for processing HL7 protocol compatible data, according to invention principles.

A system adaptively processes HL7 transaction message data and supports authoring, editing, transmitting and receiving HL7 transaction message data. The system provides support for different versions of HL7 data (including versions 2.x and 3.x (XML), for example). The system employs programming objects used to represent HL7 transactions that are advantageously exposed for use by other executable applications and in one embodiment employs components including an HL7 Examiner processor, HL7 Receiver processor and an HL7 Sender processor. The system advantageously converts HL7 transaction messages between versions including version 2.x and 3.x (XML) and provides an organized log of transactions for the documentation of interface operation or recording test results. The system also provides templates of HL7 transaction messages for generating test data in multiple versions (2.x and 3.x) and validates different HL7 transaction message versions (including 2.x and 3.x versions) by comparing a transaction with stored message definitions and embedded/external definitions (e.g., Data Type Definitions—DTDs and schemas). The system also adaptively employs Application Programming Interfaces API's for generation and parsing of HL7 transactions and stores the APIs for distribution and use by different executable applications.

A processor, as used herein, operates under the control of an executable application to (a) receive information from an input information device, (b) process the information by manipulating, analyzing, modifying, converting and/or transmitting the information, and/or (c) route the information to an output information device. A processor may use, or comprise the capabilities of, a controller or microprocessor, for example. The processor may operate with a display processor or generator. A display processor or generator is a known element for generating signals representing display images or portions thereof. A processor and a display processor may comprise a combination of, hardware, firmware, and/or software.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, subroutine, or other distinct section of code or portion of an executable application for performing one or more particular processes. These processes may include receiving input data and/or parameters, performing operations on received input data and/or performing functions in response to received input parameters, and providing resulting output data and/or parameters.

A user interface (UI), as used herein, comprises one or more display images, generated by a display processor enabling user interaction with a processor or other device and associated data acquisition and processing functions. The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of the executable procedure or executable application manipulates the UI display images in response to the signals received from the input devices. In this way, the user interacts with the display image using the input devices, enabling user interaction with a processor or other device. The activities herein may be performed automatically or wholly or partially in response to user command. An automatically performed activity is performed in response to machine instruction or operation without direct user interaction in initiating the activity.

FIG. 1 shows a system 10 for processing HL7 protocol compatible data. An interface (in HL7 receiver) 20 establishes a communication link enabling acquisition of HL7 compatible transaction messages and stores received messages in repository 19. HL7 receiver 20 establishes the communication link using, a predetermined IP address and a predetermined communication port identifier, for example. An acquisition processor (in HL7 receiver) 20 acquires multiple different HL7 compatible transaction messages including healthcare data using the communication link. An HL7 data processor (HL7 examiner) 15 automatically parses an HL7 compatible transaction message to identify HL7 items indicating type of information conveyed. The HL7 items indicate type of information conveyed including, an HL7 compatible Segment identifier, an HL7 compatible Field identifier and an HL7 compatible Component, for example. HL7 Examiner 15 operating in conjunction with HL7 sender 25 adaptively routes acquired HL7 compatible transaction messages to multiple different storage destinations based on the identified HL7 items in response to predetermined information associating HL7 items and type of information conveyed with corresponding storage destinations. HL7 examiner 15, sender 25 and receiver 20 units are controlled and inter-communicate via control unit 30 which also provides data to workstation 40 including a display processor. The display processor initiates generation of data representing at least one display image enabling a user to enter data indicating at least one of, (a) the predetermined IP address and (b) the predetermined communication port identifier. A display image also enables a user to enter the predetermined information. A filter in HL7 examiner 15 adaptively routes acquired HL7 compatible transaction messages to multiple different storage destinations based on user entered criteria.

HL7 Examiner 15 accelerates HL7 transaction message processing and reduces error involved in the processing by partitioning a transaction message into individual elements having a hierarchical structure stored in repository 17 that facilitates navigation and data validation. HL7 Examiner 15 automatically validates a transaction message by comparing a message with requirements of the HL7 standard to reduce error and facilitates accurately identifying and reporting irregularities in HL7 transaction message data. Further, HL7 Receiver 20 and HL7 Sender 25 facilitate development and testing data interfaces by emulating a sending or receiving system. System 10 automatically organizes files of transaction message data and enables re-distribution of API's stored in repository 17 for use by multiple applications. The application code in repository 17 is used by HL7 Examiner 15 for determining HL7 transaction message definitions, to generate and validate outbound HL7 transaction messages, or parse and partition inbound messages into an easy to use object model structure.

System 10 supports and accelerates development, test and operation of HL7 communication interfaces and reduces tedious error prone manual processes involved. System 10 allows a user to initiate generation of HL7 transaction messages, convert messages between different HL7 versions and check transaction message data validity and compatibility with the HL7 standard. Specifically, the system supports HL7 version 2.x and version 3.x (XML) transaction message creation and processing as well as validation of different version transaction messages against stored message definitions compatible with the HL7 standard and embedded/external Data Type Definitions (DTDs) and schemas. The system also provides message templates of HL7 transactions for generating test data in multiple versions. In addition, system 10 emulates transaction message receiving and sending functions to facilitate communication interface test and development when a receiving or sending application is not available. System 10 further provides an organized log of transactions for the documentation of test results and centrally accessible API's for generation and parsing of HL7 transactions for use by multiple different applications.

Figure 2:
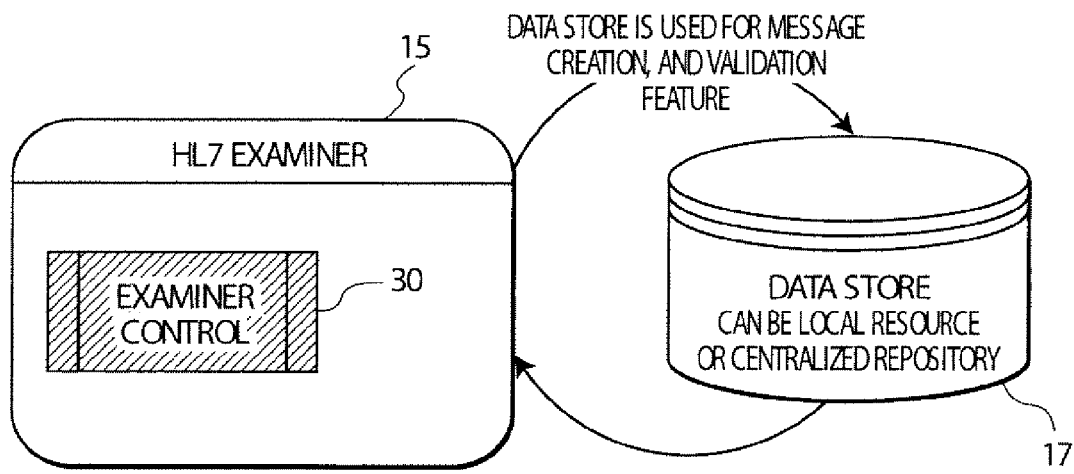
FIG. 2 shows an HL7 Examiner processor for parsing, creating editing and validating HL7 compatible transaction messages of different HL7 version, according to invention principles.
Figure 5:
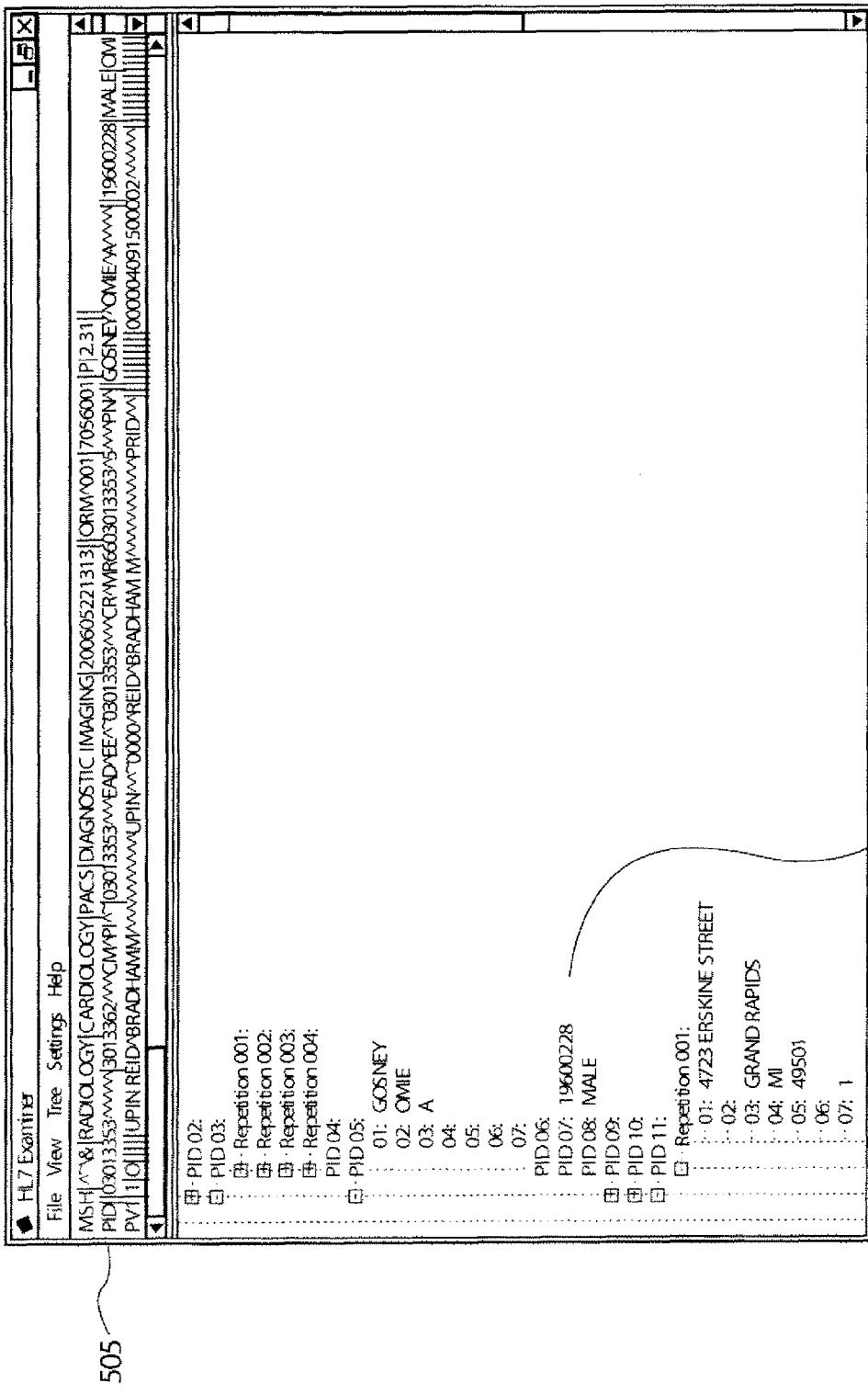
FIG. 5 shows a user interface display image presenting an HL7 message in a hierarchical structure provided by an HL7 Examiner processor, according to invention principles.

FIG. 2 shows HL7 Examiner processor 15 for parsing, creating, editing and validating HL7 compatible transaction messages of different HL7 version. HL7 examiner 15 under direction of control unit 30, employs repository 17 (a local or centralized repository) for transaction message creation and validation. A centralized repository 17 may be used in one embodiment to share definitions, templates and data tables across one or more organizations, for example. HL7 Examiner 15 supports creating and updating HL7 version 2.x and 3.x (XML) compatible transaction messages. HL7 examiner 15 automatically processes transaction messages in a file or in the form of text entered into an editor and parses, identifies and extracts HL7 items indicating type of information conveyed in an HL7 transaction message for incorporation in a hierarchical structure representing the HL7 transaction. The hierarchical structure facilitates rapid specific access to any portion of an HL7 transaction message. FIG. 5 shows a user interface display image presenting an HL7 message in a hierarchical structure provided by HL7 Examiner processor 15. Specifically, the FIG. 5 display image illustrates a transaction message in area 505 processed by Examiner 15 to provide data items of the message in a hierarchical structure representing the message in window 503.

HL7 Examiner 15 identifies HL7 items (data fields) indicating type of information conveyed including, an HL7 compatible Segment identifier, an HL7 compatible Field identifier and an HL7 compatible Component, for example, by ordinal position within individual segments. Examiner 15 also uses alternate field identification such as field name and provides an overlay of field names corresponding to data items and displays the field names in an overlay for presentation with the hierarchical data structure indicated in window 503. Window 503 also presents additional information available for each data item in a transaction message including information indicating, data type, whether an item is required/optional, name, length and a link to value tables if applicable. Further, HL7 Examiner 15 and an associated user interface image enables search within a transaction message as well as editing of, and addition to, message data in a parsed transaction message. Such editing includes an ability to de-identify, and re-populate transaction data elements with unique pre-defined data element values stored in data repository 17.

HL7 examiner 15 supports creation of transaction messages of a user selected HL7 standard version through enabling definition of user-defined table values and creation of new (empty) messages compatible with an HL7 specification. Examiner 15 enables a user or system to select a Message Type, Trigger Event, and HL7 version for generation of an empty message template. A message template is generated based on message type or segment identifier with default value sets for message elements and a definition of data items (elements) to be removed from the message or segment. Further, a generated template transaction message is populated with unique pre-determined or user-defined data values aiding compliance with HIPAA (Healthcare Information Portability & Accountability Act) regulations. Data items of generated transaction messages (and received messages) are validated by comparison with an HL7 version 2.x message definition, embedded or external XML DTDs, or schemas (version 2.x or 3.x) as well as user defined HL7 tables. The HL7 and other transaction message standards, user templates, and user defined tables are stored in local or centralized data repository 17.

Examiner 15 is integrated with HL7 Sender 25 enabling transaction messages to be communicated dynamically and Examiner 15 converts HL7 transaction messages from one HL7 standard version to another. In addition unit 15 migrates data from a transaction message of one version to a comparable transaction in another specified HL7 version and alerts a user to elements in transaction that could not be migrated. Application Programming Interfaces (APIs), data determining message format standards, user determined templates, and user defined tables are stored in a centralized repository (e.g., repository 17) that are used to facilitate application HL7 interface programming and reduce the burden of parsing and message generation from executable application code. Examiner 15 accesses data objects comprising HL7 data nodes accessible by field name, or number and indicating object hierarchical structure including parent, child and sibling objects and data items and whether a validation process indicates that an error is associated with a data object. These features advantageously enable users to create HL7 compatible data interfaces without needing detailed familiarity with the HL7 standard.

Figure 3:
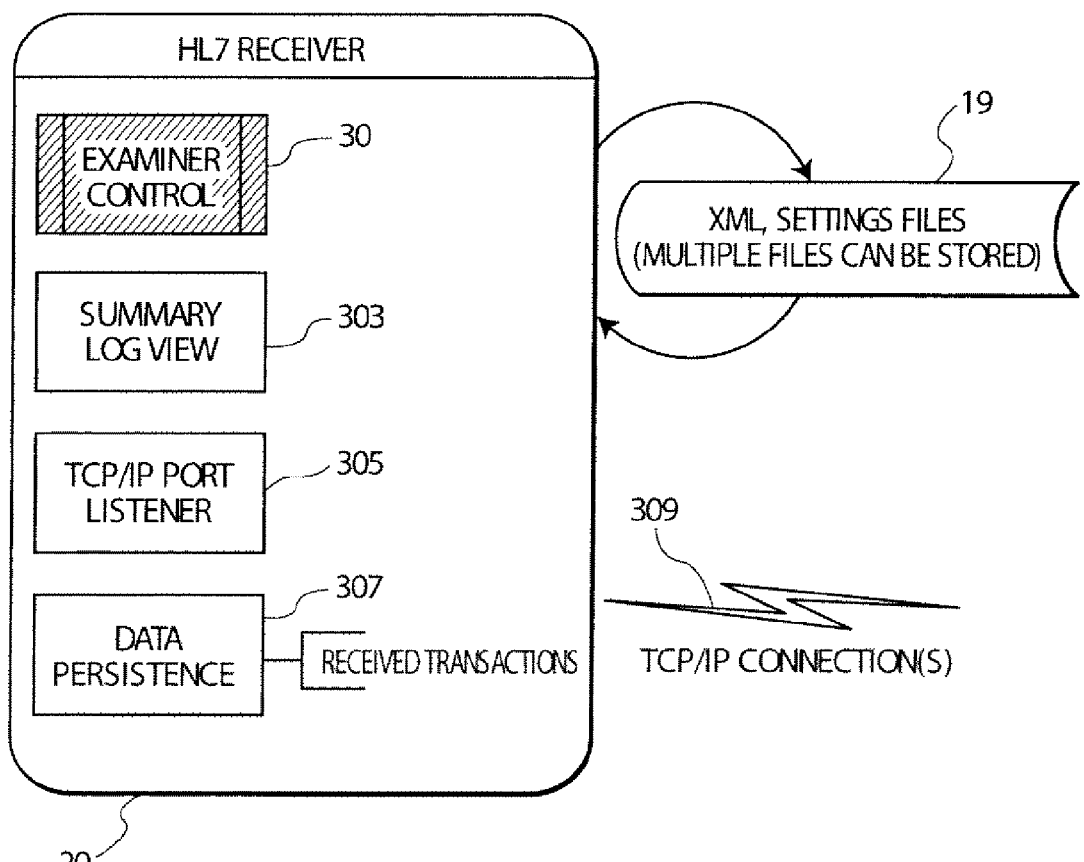
FIG. 3 shows an HL7 Receiver processor for receiving and displaying received HL7 compatible transaction messages of different HL7 version, according to invention principles.
Figure 6:
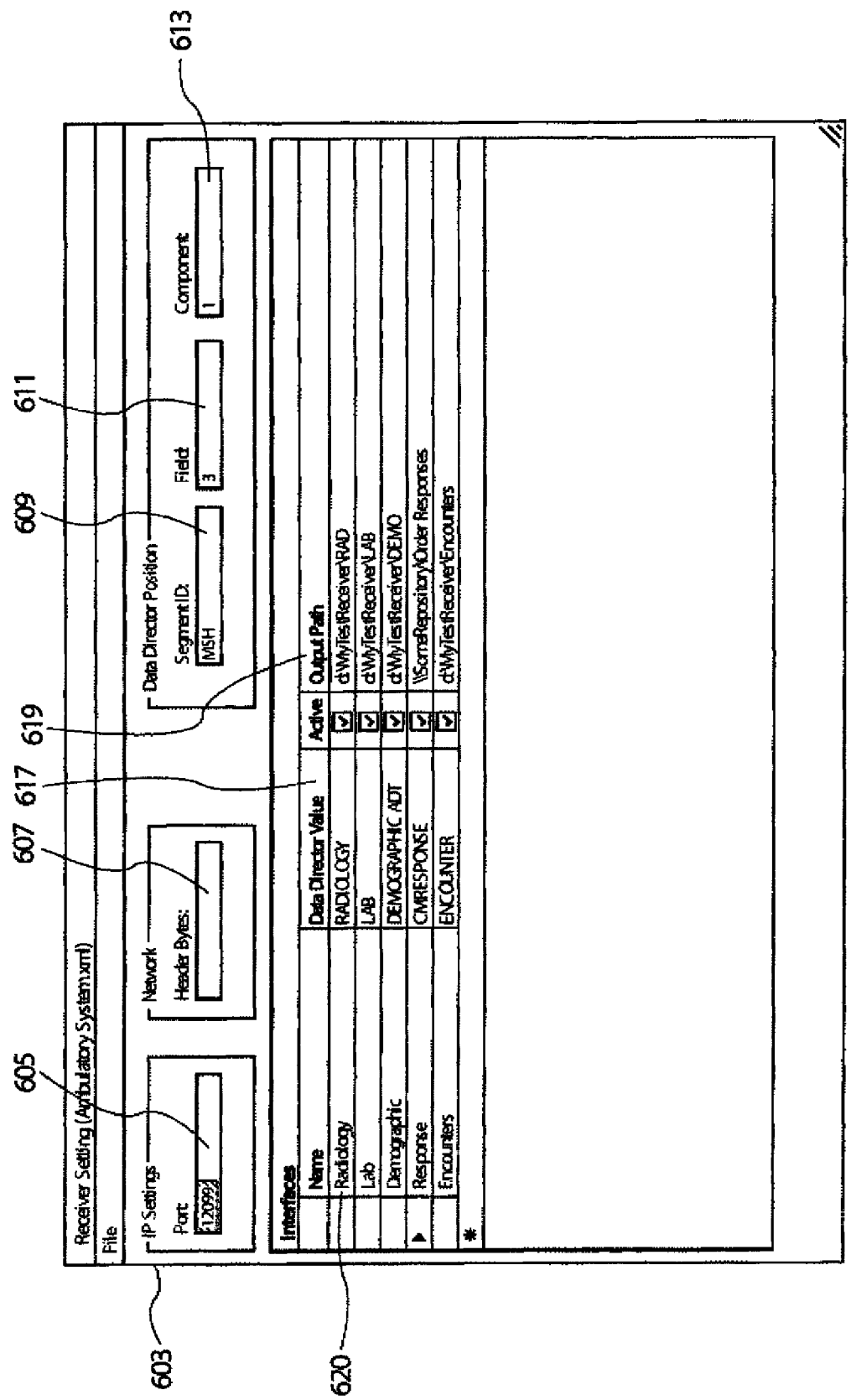
FIG. 6 shows a user interface display image illustrating HL7 Receiver processor settings, according to invention principles.

FIG. 3 shows HL7 Receiver processor 20 for receiving and displaying received HL7 compatible transaction messages of different HL7 version that is configured using an XML file loaded from repository 19 in response to user command. The XML file is defined by a user via a Receiver Settings display image displayed on workstation 40. Further, multiple setting files can be stored to re-configure Receiver 20 for a particular task. FIG. 6 shows user interface display image 603 illustrating selection of HL7 Receiver processor settings. Specifically, image 603 illustrates selection of settings including, port(s) in box 605 on which Receiver port listener 305 (FIG. 3) listens for a connection. Multiple ports can be specified in the settings file and Receiver 20 instantiates a listening process for each port specified. Box 607 enables selection of a Network header (header bytes) if desired and a header may be stripped from a transaction message or stored with a transaction message, in response to predetermined configuration information. Master Data filter position elements entered in boxes 609, 611 and 613 determine a location within a transaction message that is parsed at which data items are found for use in processing the transaction message. Specifically, boxes 609, 611 and 613 determine an HL7 compatible message location comprising, Segment ID, Field (ordinal position for 2.x HL7 messages, a node determined by name and data type for 3.x HL7 messages) and Component (ordinal position for 2.x HL7 messages, a node determined by name and data type for 3.x HL7 messages), respectively. The Segment ID, Field and Component are used by Receiver 20 to identify a location in a transaction message examined to find a Data Director Value listed in column 617 (FIG. 6). A transaction message having a Data Director Value matching a value in column 617 is stored in a corresponding storage location indicated in column 619 in repository 307 (FIG. 3). For example, row 620 indicates a transaction message having a Data Director Value of RADIOLOGY is stored in a location via path d:\MyTestReceiver\RAD.

Figure 7:
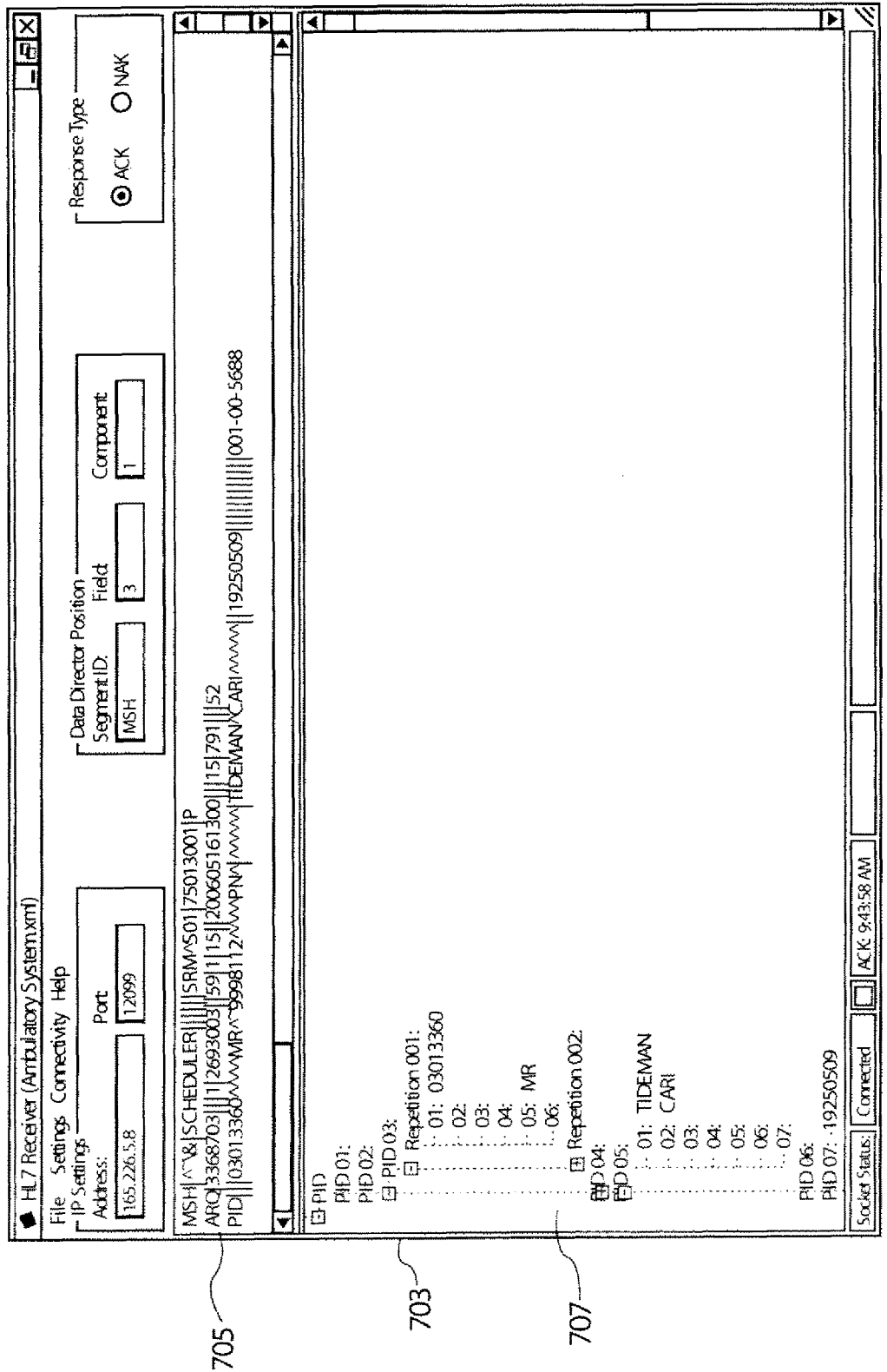
FIG. 7 shows a user interface display image presenting an HL7 message in a hierarchical structure provided by an HL7 Receiver processor, according to invention principles.

Thereby Receiver 20 filters transaction messages and the identified transaction messages are stored in disk locations indicated by corresponding matching Data Director Value criteria. Individual interface settings 609, 611 and 613 used to locate a data item, can create 1 . . . n sub data filter definitions to further isolate transactions and route them to different storage locations. As each transaction is received, Receiver 20 sends a response via a current connection. The Receiver sends one of the following responses: HL7 ACK (HL7 version 2.x and 3.x) and HL7 NAK (HL7 version 2.x and 3.x) via communication (e.g., TCP/IP) link 309. If a transaction message is a custom message, no response is generated. Receiver 20 initiates display of summary view display image 303 (FIG. 3) of transactions received during a communication connection via workstation 40 (FIG. 1). Summary view display image 303 allows a user to see file logs written to a disk and reconcile the number of transactions received. A Log entry in image 303 may be selected to open an associated transaction message file and load it for processing by an instance (executing copy) of HL7 Examiner 20. A user employs Examiner control unit 30 to specify a string that is used to scan transaction files and filter the log and also initiate a search of transaction messages. Further, HL7 Receiver 20 may display a detailed view via workstation 40 of the last transaction received during a communication link connection. FIG. 7 shows user interface display image 703 presenting an HL7 message in a hierarchical structure provided by HL7 Receiver 20. Image 703 shows a hierarchical structure in window 707 corresponding to a last transaction message having Segment ID, Field and Component values 705. HL7 Examiner control unit 30 provides image 703 displaying the illustrated parsed transaction message data items.

Figure 4:
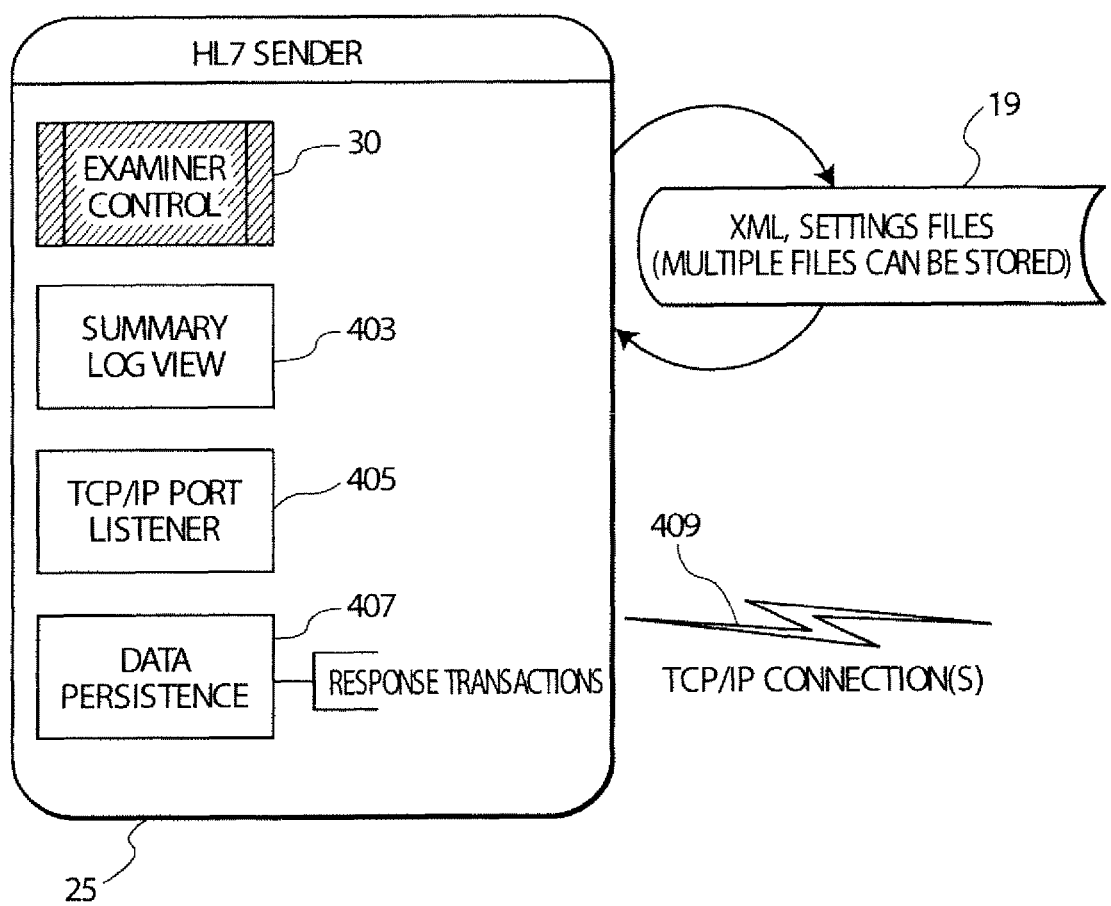
FIG. 4 shows an HL7 Sender processor for sending and displaying sent HL7 compatible transaction messages of different HL7 version, according to invention principles.

FIG. 4 shows HL7 Sender processor 25 for sending and displaying sent HL7 compatible transaction messages of different HL7 version. HL7 Sender 25 including TCP/IP port connector 405 enables a user to send transaction messages to a receiving system or an integration engine via communication (e.g., TCP/IP compatible) link 409. HL7 Sender 25 configuration settings are loaded from an XML file retrieved from repository 19 or HL7 sender 25 may be configured manually via a user interface image presented on workstation 40. HL7 Sender 25 Settings include, an IP address of a device receiving a transaction message, a Port for communication and an Acknowledgment setting determining whether Sender 25 is to wait for a response before sending additional transaction messages (if queued). HL7 Sender 25 Settings also include, a Log response path whereupon, if the path is set, unit 407 logs responses from a receiving system and Header information including a Header Length in bytes which is set to zero if no header is desired. A Last/Not Last indicator is used to indicate a last transaction message.

An image display summary view 403 presented on workstation 40 displays transaction messages sent and responses received, through connection 409 and enables a user to view response logs written to disk. Summary view 403 enables a user to select a particular log entry to open an associated file and load it for processing by an instance of HL7 Examiner 15. HL7 Sender 25 further enables a user to specify a string that is used to scan response files and filter data items for presentation in summary window 403. Summary view 403 further displays a list of transaction message files queued to be sent. The list can be sorted or manually ordered for specific transaction message progression testing. In response to user selection of a transaction message file from the list, a detail view of the transaction message is displayed where it can be dynamically edited and saved, or left in memory for a one time or temporary modification. Summary view 403 may also comprise a detail view display of a last transaction sent by HL7 Sender 25. In one embodiment the last transaction message is parsed, processed and displayed in a hierarchical view provided by HL7 Examiner 15 and enabling search of the message as directed by control unit 30.

System 10 advantageously provides transaction message data conversion between different HL7 release versions and creates transaction messages using standard message layouts and user templates. The created messages are populated using data elements from predetermined or user-determined acceptable data values for transaction messages and comply with user determinable organization criteria. System 10 further performs validation of HL7 transaction messages including version 2.x and 3.x transaction messages by comparison with stored message definitions and embedded or external Data Type Definitions and schemas, for example and simulates a system endpoint such as a receiving or sending system.

HL7 Examiner 15 and HL7 Sender 25 are usable in providing an inbound interface to a receiving system and HL7 Receiver 20 and HL7 Examiner 15 are usable to help test an outbound interface from a sending system, for example. System 10 is usable by a hospital and healthcare facilities to process and support build, test, and validate messages. The system employs API's for building and deploying HL7 interfaces within an application and facilitates healthcare integration of HL7 applications. In a healthcare application, system 10 is usable to test an integration engine map supporting exchanging transaction messages between different computer systems. Such an integration engine and map is used for conveying laboratory test results between an ambulatory electronic medical record and a clinical repository, for example.

Figure 8:
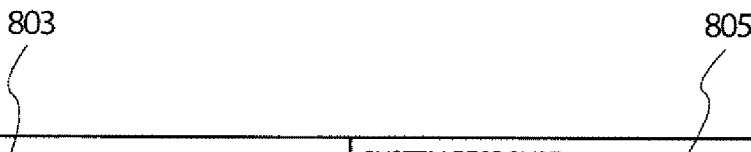
FIG. 8 shows system user interactive operations and system response involved in providing an HL7 inbound message interface to a receiving system, according to invention principles.
Figure 9:
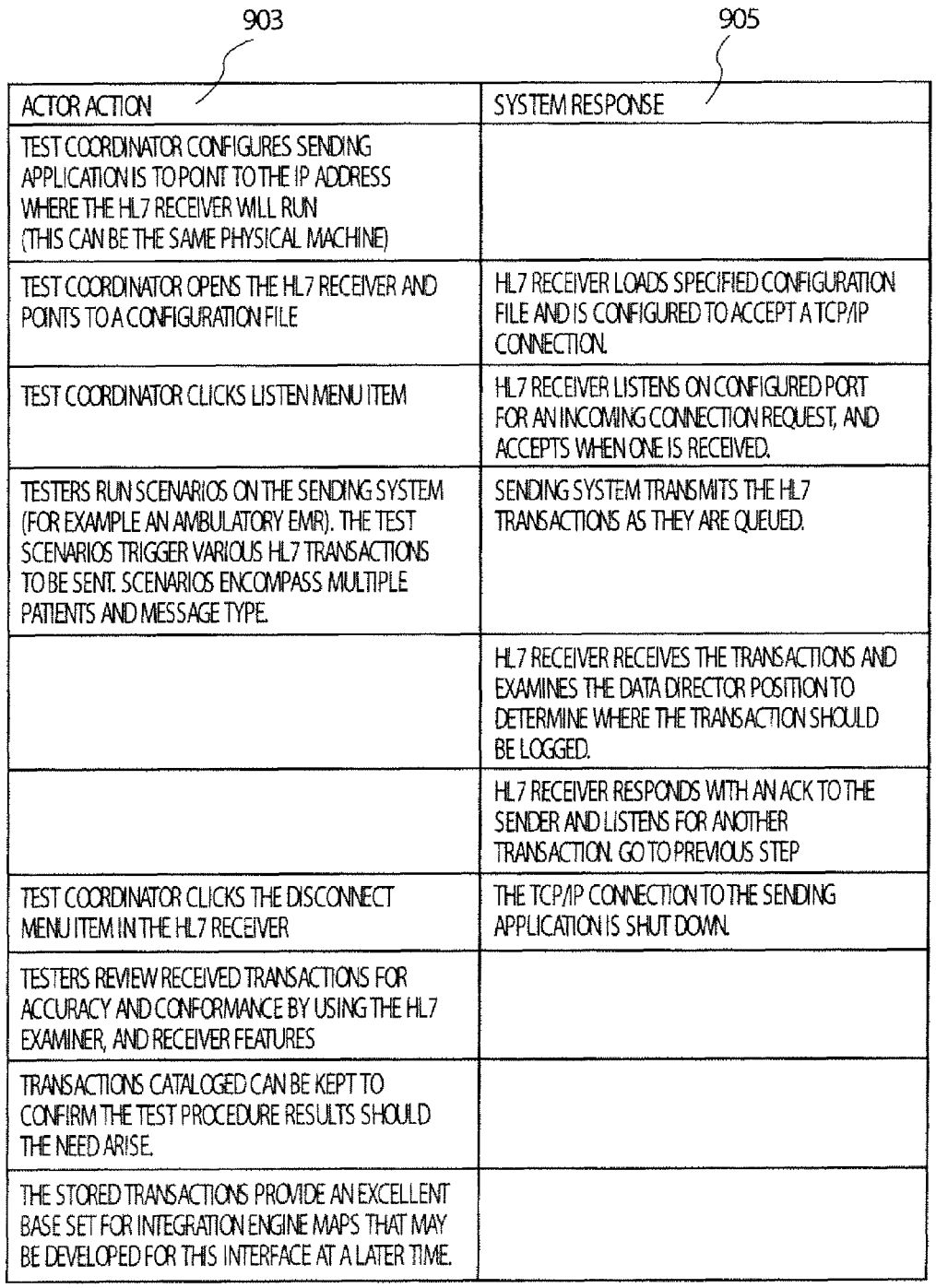
FIG. 9 shows system user interactive operations and system response involved in providing and testing an HL7 outbound message interface from a sending system, according to invention principles.

FIG. 8 shows system user interactive operations and system responses involved in providing an HL7 inbound message interface to a receiving system. Column 803 indicates user actions and column 805 indicates corresponding system 10 responses in providing an inbound message interface to a receiving system. FIG. 9 shows system user interactive operations and system responses involved in providing and testing an HL7 outbound message interface from a sending system. Column 903 indicates user actions and column 905 indicates corresponding system 10 responses in providing and testing an HL7 outbound message interface from a sending system. FIG. 10 shows system user interactive operations and system response involved in providing and testing an integration engine HL7 message interface between an ambulatory system and a clinical information repository. Column 923 indicates user actions and column 925 indicates corresponding system 10 responses in providing and testing an integration engine HL7 message interface between an ambulatory system and a clinical information repository. FIG. 11 shows system user interactive operations and system response involved in employing an API in providing and testing an HL7 message interface. Column 933 indicates user actions and column 935 indicates corresponding system 10 responses involved in employing an API in providing and testing an HL7 message interface.

Figure 12:
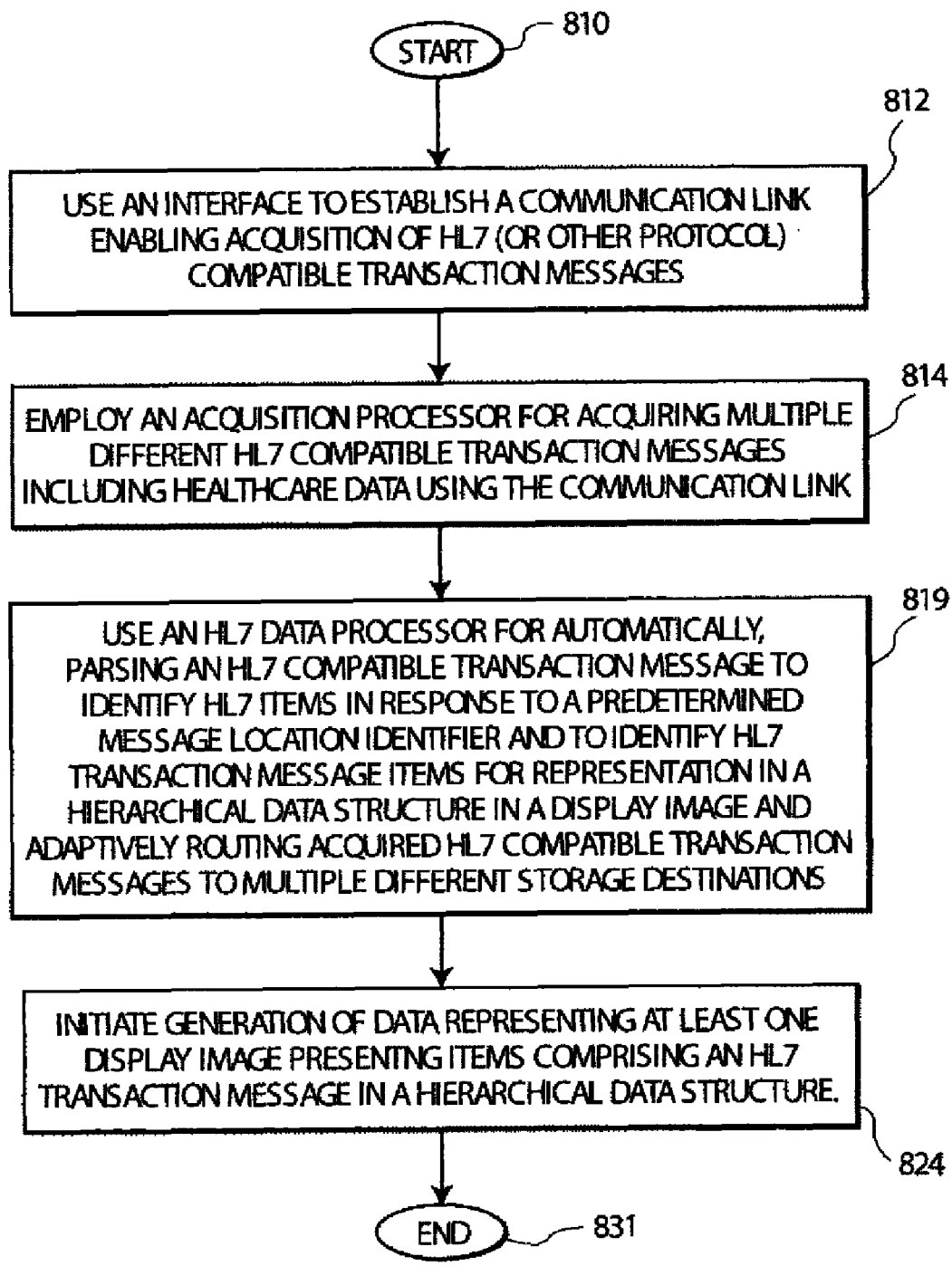
FIG. 12 shows a flowchart of a process performed by a system for processing HL7 protocol compatible data, according to invention principles.

FIG. 12 shows a flowchart of a process performed by system 10 (FIG. 1) for processing HL7 (or other) protocol compatible data. In step 812 following the start at step 810, an interface (in HL7 receiver) 20 establishes a communication link enabling acquisition of HL7 compatible transaction messages using a predetermined IP address and a predetermined communication port identifier. In step 814 an acquisition processor (in HL7 receiver) 20 acquires multiple of different HL7 compatible transaction messages including healthcare data using the communication link. An HL7 data processor (HL7 examiner) 15 in step 819 automatically, parses an HL7 compatible transaction message to identify HL7 items indicating type of information conveyed at a location in the transaction message identified in response to a predetermined message location identifier and to identify HL7 transaction message items for presentation in a hierarchical data structure in a display image. The predetermined message location identifier comprises one or more of, an HL7 compatible Segment identifier, an HL7 compatible Field identifier and an HL7 compatible Component. A filter in HL7 examiner 15 adaptively routes acquired HL7 compatible transaction messages to multiple different storage destinations based on the identified HL7 items indicating type of information conveyed in response to predetermined information (e.g., comprising user entered criteria) associating HL7 items and type of information conveyed with corresponding storage destinations.

In step 824 a display processor in system 10, e.g., in one or more of units 15, 20, 25 and 40 initiates generation of data representing at least one display image reproduced on workstation 40 presenting items comprising a received or sent HL7 transaction message (e.g., a last transaction message sent) in a hierarchical data structure. Further display images present a list of transaction messages received or sent over a predetermined time period and enable a user to enter data indicating the predetermined IP address and the predetermined communication port identifier through which the communication link is established. Additional display images enable a user to enter the predetermined message location identifier and enable a user to enter the predetermined information associating HL7 items and type of information conveyed with corresponding storage destinations. Also the display images enable a user to enter data for identifying at least a portion of a transaction message header and to enter data indicating at least a portion of a transaction message header is to be removed from a transaction message before storage or a transaction message is to be stored with header data. The process of FIG. 12 terminates at step 831.

The system, processes and image displays of FIGS. 1-12 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system for processing HL7 protocol (or other protocol) compatible data processes and support build, test, and validate messages. The processes and applications provided by system 10 (FIG. 1) may in alternative embodiments, be located on one or more (e.g., distributed) processing devices accessing a network linking the FIG. 1 elements or that are remotely accessible. Further, any of the functions and steps provided in FIGS. 1-12 may be implemented in hardware, software or a combination of both.

What is claimed is:

1. A system for processing HL7 protocol compatible data, comprising:
an interface for establishing a communication link enabling acquisition of HL7 compatible transaction messages;
an acquisition processor for acquiring a plurality of different HL7 compatible transaction messages including healthcare data using said communication link; and
an HL7 data processor for automatically,
parsing an HL7 compatible transaction message to identify HL7 items indicating type of information conveyed at a location in said transaction message identified in response to a predetermined message location identifier,
migrating data from said transaction message of one HL7 version to a corresponding transaction message in another HL7 version and
adaptively routing acquired HL7 compatible transaction messages of one or more HL7 versions to a plurality of different storage destinations based on the identified HL7 items indicating type of information conveyed in response to predetermined information associating HL7 items and type of information conveyed with corresponding storage destinations and said HL7 data processor generates an alert identifying elements in said transaction message that could not be migrated.

2. A system according to claim 1, wherein
said predetermined message location identifier comprises an HL7 compatible Segment identifier.

3. A system according to claim 2, wherein
said predetermined message location identifier comprises at least one of, (a) an HL7 compatible Field identifier and (b) an HL7 compatible Component.

4. A system according to claim 1, wherein
said interface establishes said communication link using at least one of, (a) a predetermined IP address and (b) a predetermined communication port identifier.

5. A system according to claim 4, including
a display processor for initiating generation of data representing at least one display image enabling a user to enter data indicating at least one of, (a) said predetermined IP address and (b) said predetermined communication port identifier.

6. A system according to claim 1, including
a display processor for initiating generation of data representing at least one display image enabling a user to enter said predetermined message location identifier.

7. A system according to claim 1, including
a display processor for initiating generation of data representing at least one display image enabling a user to enter said predetermined information associating HL7 items and type of information conveyed with corresponding storage destinations.

8. A system according to claim 1, including
a filter for adaptively routing acquired HL7 compatible transaction messages to a plurality of different storage destinations based on user entered criteria comprising said predetermined information associating HL7 items and type of information conveyed with corresponding storage destinations.

9. A system according to claim 1, including
a display processor for initiating generation of data representing at least one display image enabling a user to enter a port identifier for identifying a port through which said communication link is established.

10. A system according to claim 1, including
a display processor for initiating generation of data representing at least one display image enabling a user to enter data for identifying at least a portion of a transaction message header.

11. A system according to claim 10, wherein
said at least one display image enables a user to enter data indicating at least a portion of a transaction message header is to be at least one of, (a) removed from a transaction message before storage and (b) a transaction message is to be stored with header data.

12. A system for processing HL7 protocol compatible data, comprising:
an interface for establishing a communication link enabling acquisition of transaction messages compatible with a protocol;
an acquisition processor for acquiring a plurality of different transaction messages compatible with said protocol including healthcare data using said communication link;
a data processor for automatically,
parsing a transaction message compatible with said protocol to identify items indicating type of information conveyed at a location in said transaction message identified in response to a predetermined message location identifier and to identify transaction message items for presentation in a hierarchical data structure in a display image, migrating data from said transaction message of one HL7 version to a corresponding transaction message in another HL7 version and adaptively routing acquired transaction messages of one or more HL7 versions compatible with said protocol to a plurality of different storage destinations based on the identified items indicating type of information conveyed in response to predetermined information associating items and type of information conveyed with corresponding storage destinations and said data processor generates an alert identifying elements in said transaction message that could not be migrated; and a display processor for initiating generation of data representing at least one display image presenting items comprising a transaction message compatible with said protocol in a hierarchical data structure.

13. A system according to claim 12, wherein said protocol comprises HL7 protocol.

14. A system according to claim 12, wherein said display processor initiates generation of data representing at least one display image presenting at least one of, (a) a list of transaction messages sent and (b) a last transaction message sent.

15. A system according to claim 14, wherein said display processor initiates generation of data representing at least one display image presenting a hierarchical data structure of a last transaction message sent.

16. A system for processing HL7 protocol compatible data, comprising:

an interface for establishing a communication link enabling acquisition of HL7 compatible transaction messages;

an acquisition processor for acquiring a plurality of different HL7 compatible transaction messages including healthcare data using said communication link;

an HL7 data processor for automatically, parsing an HL7 compatible transaction message to identify HL7 items indicating type of information conveyed at a location in said transaction message identified in response to a predetermined message location identifier and to identify HL7 transaction message items for presentation in a hierarchical data structure in a display image migrating data from said transaction message of one HL7 version to a corresponding transaction message in another HL7 version and adaptively routing acquired HL7 compatible transaction messages of one or more HL7 versions to a plurality of different storage destinations based on the identified HL7 items indicating type of information conveyed in response to predetermined information associating HL7 items and type of information conveyed with corresponding storage destinations and said HL7 data processor generates an alert identifying elements in said transaction message that could not be migrated; and a display processor for initiating generation of data representing at least one display image presenting items comprising an HL7 transaction message in a hierarchical data structure.

* * * * *